(12) United States Patent
Albert et al.

(10) Patent No.: US 7,507,528 B2
(45) Date of Patent: *Mar. 24, 2009

(54) METHOD AND DIAGNOSIS KIT FOR SELECTING AND OR QUALITATIVE AND/OR QUANTITATIVE DETECTION OF CELLS

(75) Inventors: Winfried Albert, Penzberg (DE); Pia Steffens, Hannover (DE); Alf-Andreas Krehan, Anzing (DE); Stefanie Waschuetza, Hannover (DE)

(73) Assignee: Adnagen AG, Hannover-Langenhagen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/488,729

(22) PCT Filed: May 17, 2002

(86) PCT No.: PCT/EP02/05489

§ 371 (c)(1),
(2), (4) Date: Sep. 20, 2004

(87) PCT Pub. No.: WO03/023057

PCT Pub. Date: Mar. 20, 2003

(65) Prior Publication Data

US 2005/0042685 A1 Feb. 24, 2005

(30) Foreign Application Priority Data

| Sep. 6, 2001 | (DE) | 101 43 691 |
| Sep. 6, 2001 | (DE) | 101 43 699 |
| Sep. 6, 2001 | (DE) | 101 43 775 |
| Sep. 6, 2001 | (DE) | 101 43 776 |

(51) Int. Cl.
C12Q 1/68 (2006.01)
G01N 33/574 (2006.01)

(52) U.S. Cl. ............ 435/6; 435/7.2; 435/7.23; 435/30; 435/91.2; 435/91.21

(58) Field of Classification Search .......... 435/2.6, 435/7.2, 7.23, 30, 91.2, 91.21, 325, 366, 435/371, 267, 269, 975, 810
See application file for complete search history.

(56) References Cited

U.S. PATENT DOCUMENTS

| 5,336,760 | A | 8/1994 | Hardwick et al. |
| 6,033,574 | A | 3/2000 | Siddiqi |
| 6,165,467 | A | 12/2000 | Hagiwara et al. |
| 6,187,546 | B1 * | 2/2001 | O'Neill et al. ............ 435/7.1 |
| 7,056,660 | B1 * | 6/2006 | Giesing et al. ............ 435/6 |
| 2002/0058255 | A1 * | 5/2002 | Thum et al. ............ 435/6 |

FOREIGN PATENT DOCUMENTS

| DE | 29 52 815 C1 | 5/1985 |
| DE | 38 11 659 C1 | 11/1989 |
| DE | 197 36 691 A1 | 2/1999 |
| EP | 0 520 794 A1 | 12/1992 |
| JP | 61-189454 A | 8/1986 |
| JP | 2000-254472 A | 9/2000 |
| WO | WO 94/07139 A1 | 3/1994 |
| WO | WO 96/29430 A1 | 9/1996 |
| WO | WO 97/07242 A1 | 2/1997 |
| WO | WO 97/35589 A1 | 10/1997 |
| WO | WO 97/37226 A1 | 10/1997 |
| WO | WO 97/38313 | 10/1997 |
| WO | WO 98/12227 A1 | 3/1998 |
| WO | WO 99/10528 | 3/1999 |
| WO | WO 99/44064 A1 | 9/1999 |
| WO | WO 03/023057 A2 | 3/2003 |
| WO | WO 03/023059 A2 | 3/2003 |
| WO | WO 03/023060 A3 | 3/2003 |
| WO | WO 03/044224 A1 | 5/2003 |

OTHER PUBLICATIONS

Balzar et al., *J Mol Med*, 77, 699-712 (1999).
Burchill et al., *British Journal of Cancer*, 71, 278-281 (1995).
Charpentier et al., *Cancer Research*, 60 (21), 5977-5983 (2000).
Charpentier et al., *Proceedings of the American Association for Cancer Research*, 42, 3378 (2001).
Chrysogelos et al., *Breast Cancer Research and Treatment*, 29, 29-40 (1994).
Coltrera et al., *Cancer Research*, 55, 2703-2708 (1995).
Cui et al., *World J Gastroenterol*, 7 (3), 381-386 (2001).
De Luca et al., *Clinical Cancer Research*, 6, 1439-1444 (2000).
Fathi et al., *Journal of Biological Chemistry*, 268 (8), 5979-5984 (1993).

(Continued)

Primary Examiner—David A Saunders
(74) Attorney, Agent, or Firm—Fulbright & Jaworski, LLP

(57) ABSTRACT

This invention relates to a method for selecting and/or for qualitative and/or quantitative detection of predetermined biological cells from or in a sample containing biological cells, the sample being mixed with a predetermined combination of at least two antibodies and/or antibody derivatives, which bind preferentially with their binding sites to different epitopes of the cells to be selected or detected, and/or with at least one biospecific antibody and/or antibody derivative, which binds preferentially with its two binding sites to different epitopes of the cells to be selected or detected, which are separated from the sample with cells marked with at least one of the antibodies and/or antibody derivatives, and the separated cells being tested with a predetermined combination of at least two molecular-biological detection reagents, the at least two detection reagents reacting preferentially with at least one component of the cells to be selected or detected.

26 Claims, 10 Drawing Sheets

OTHER PUBLICATIONS

Figure 1:
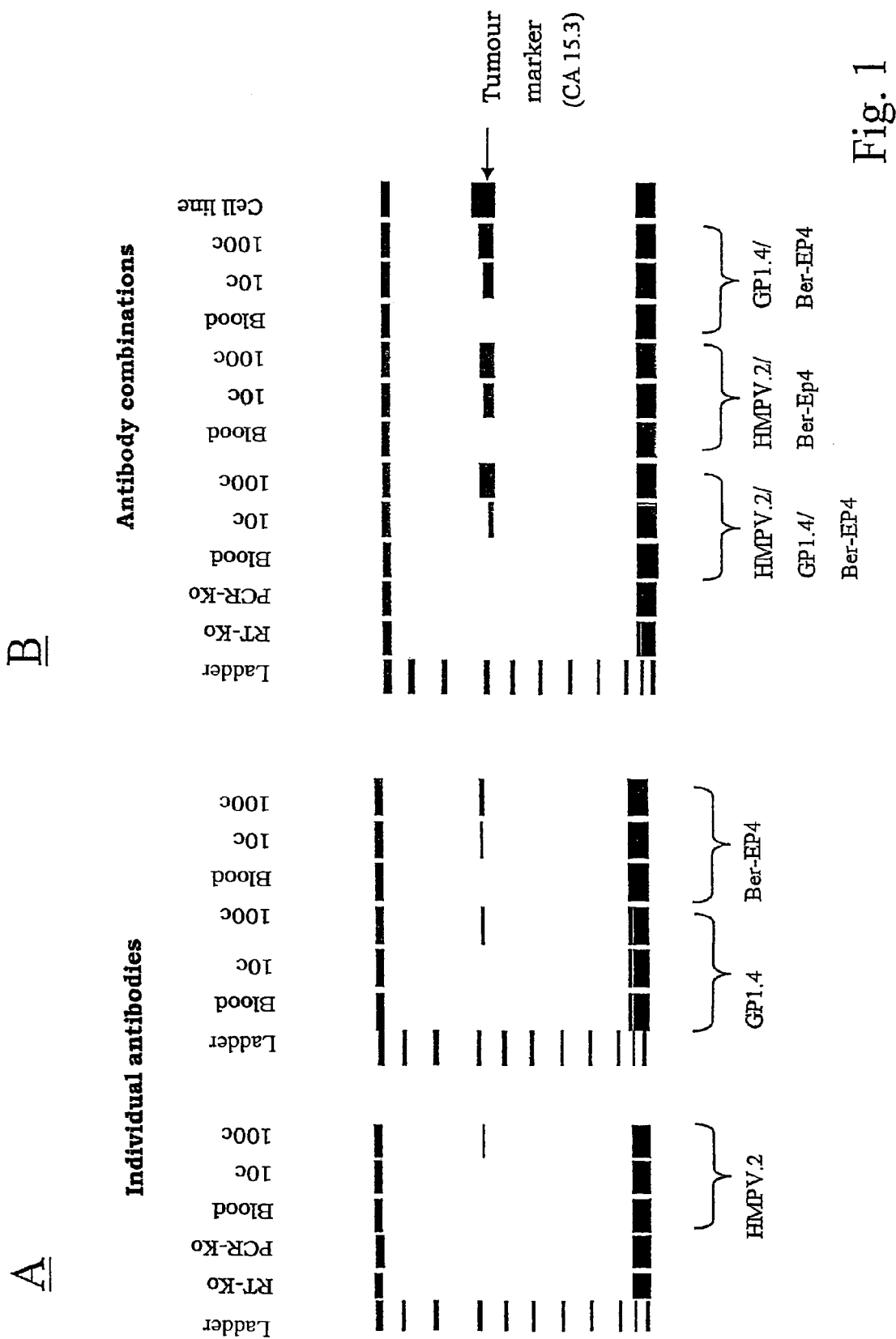

Fujiwara et al., *International Journal of Oncology*, 16, 799-804 (2000).
Ghossein et al., *Clinical Cancer Research*, 5, 1950-1960 (1999).
Gion et al., *Cancer Journal*, 7 (3), 181-190 (2001).
Hardingham et al., *Advances in Brief*, 53, 3455-3458 (1993).
Ito et al., *Virchows Archiv B Cell Pathology*, 59, 173-178 (1990).
Martin et al., *PNAS*, 98 (5), 2646-2651 (2001).
Masseyeff et al., *Methods of Immunological Analysis*, 1, 506-529 (1993).
Nacht et al., *Cancer Research*, 59, 5464-5470 (1999).
Niemeyer et al., *Angew. Chem. Int. Ed.*, 38 (19), 2865-2869 (1999).
Notterman et al., *Cancer Research*, 61, 3124-3130 (2001).
Ooka et al., *Oncology Reports*, 7 (3), 561-566 (2000).
Park et al., *Journal of Cancer Research and Clinical Oncology*, 127 (8), 489-494 (2001).
Pottek et al., *European Journal of Cancer*, 33, S43 (1997).
Racila et al., *Proc Natl. Acad. Sci*, 95, 4589-4594 (1998).
Ren-Heidenreich et al., *Human Gene Therapy*, 11, 9-19 (2000).
Smith et al., *The Lancet*, 338, 1227-1229 (1991).
Watanabe et al., *Journal of Biological Chemistry*, 264 (21), 12611-12619 (1989).
Zhong et al., *Archives of Gynecology and Obstetrics*, 263, 2-6 (1999).

* cited by examiner

METHOD AND DIAGNOSIS KIT FOR SELECTING AND OR QUALITATIVE AND/OR QUANTITATIVE DETECTION OF CELLS

This application is the U.S. National Phase of international patent application PCT/EP02/05489, filed on May 17, 2002, and claims priority to German patent application numbers 10143691.2, filed Sep. 6, 2001, 10143699.8, filed Sep. 6, 2001, 10143775.7, filed Sep. 6, 2001, and 10143776.5, filed Sep. 6, 2001 and International Patent Application PCT/EP01/13606, filed Nov. 22, 2001, all of which are hereby incorporated by reference.

The present invention relates to a method and a diagnosis kit for selecting and/or for qualitative and/or quantitative detection of cells in a sample. Detection methods and diagnosis kits of this type are required in particular in the diagnostics or treatment control of tumour diseases. Because within the scope of cancer pre- or after-care, it is of great importance to be able to detect in good time malignant tumours or recidive malignant tumours by means of the occurrence of metastasising tumour cells in the blood. The present method and the present diagnosis kit are however used not only here but can also be used very basically for detecting and recognising uncommon cells in samples containing biological cells. This can be effected for example also for detecting fetal cells in maternal blood or also for indicating stem cells.

Testicular cancer is responsible in men for less than 2% of all malignant neoformations of tumours. Admittedly, 20-30% of all cancer diseases in men under 40 concern testicular cancer. The number of annual new diseases for example in the Federal Republic of Germany is approximately 3,600, approximately 240 men dying of testicular cancer. The highest incidence is thereby found between the $25^{th}$ and $40^{th}$ year. Due to the progress in oncological therapy, today over 90% of all those affected can be cured in the long term. The high survival rates are thereby based on the distinct effectiveness of chemotherapies based on cisplatinum.

Breast cancer is the most frequent diagnosis when a tumour disease is confirmed in women (26.4% of all new diseases). Despite huge efforts, which are applied to early detection, treatment and after-care, this disease still ranks in prime position of cancer-conditioned causes of death in women. The disease numbers in western industrial countries have been increasing further in the past years despite increased efforts in early detection. What is problematic is the high metastasising rate after initial treatment which in the majority of cases already leads after 1-3 years to the death of the patient. The main reason for this is the dissemination of tumour cells in the early stages of the tumour development. In addition to the initial detection of a mammary carcinoma, that is why in particular the earliest possible indication of metastasising cells is of crucial importance for a successful treatment. Likewise, a definitive negative detection can be helpful in clinical stage 1 if a decision has to be made about whether the patient must be treated with a chemotherapy or an operation.

In the case of colorectal primary tumour, the tumour progression after resection can be attributed primarily to residual tumour cells. These cells are detached from the primary tumour preoperatively or intraoperatively and preserve the possibility of dissemination in the entire organism.

Besides initial detection of a colorectal carcinoma, in particular the earliest possible detection of metastasising cells is of crucial importance for a successful treatment.

It is thereby necessary to decide in the clinical stage 1 of the diseases whether the patient must undergo a chemotherapy and/or an operation in order to achieve a permanent successful treatment. A large number of patients is thereby treated with chemotherapy although no certain detection of a metastasis is present. In concepts which are based on pure monitoring, the result in 25% of cases is however recurrences with in part a mortal outcome.

In the case of the test methods applied at the moment, so-called tumour markers at the protein level (immunological or enzymatic) are determined quantitatively in the blood or in other body fluids in the case of cancer patients. These detection methods are however only suitable in a conditional manner for tumour diagnostics or treatment control/after-care in the case of tumours since increased tumour marker values in body fluids can also be produced by non-tumorous diseases, such as for example inflammations of the gastro-intestinal tract, liver cirrhosis, virus infections or heavy smoking.

Molecular genetic methods appear helpful here for detecting tumour cells in the peripheral blood since a crossing of tumour cells into venous blood can take place at the beginning of the metastasis process.

EP 0 520 794 B1 discloses such a method in which metastases are detected in body tissues or fluids. Nucleic acids are thereby detected, for example by means of multiplication by polymerase chain reaction. The method is decisively based now on the fact that the detected nucleic acid sequence is expressed in cells of the original tissue of a tumour, i.e. in tumour cells and also in healthy cells of the original tissue dependent upon markers. It is a further condition that this sequence is normally not expressed in those cells, the tissue of which is being examined. If therefore a corresponding sequence is found in the tested sample, then this must originate from entrained, i.e. metastasising cells of a distant tumour. Hence, this method is ultimately based on the detection of cells which should not occur in the blood sample of healthy persons.

It must be emphasised overall that the diagnostic methods used at present are too imprecise if they concern the assessment of the malignant potency of residual tumours after chemotherapy has been performed in the metastasising stages. It is furthermore necessary therefore to find indications for an occult or residual metastasis which permits classification in good time into the diverse primary curative therapeutic options. It is a substantial problem hereby that the cells to be detected, for example tumour cells in the peripheral blood, only occur in extremely low numbers.

Starting from this state of the art, it is the object of the present invention to provide a method and a diagnosis kit with which, in a simple, reliable and repeatable manner, uncommon biological cells in a sample containing biological cells can be selected and/or detected with high sensitivity and specificity.

This object preferably is achieved by the characterizing features of the present invention. Advantageous embodiments and further developments of the solution will be apparent from the description of the invention provided herein.

It is crucial now in the method according to the invention that firstly the cells to be selected or detected are marked by means of a combination of antibodies or antibody derivatives or by a bispecific antibody or antibody derivative. As a result, it is possible to mark, separate and hence concentrate in particular the sought cells. This means that, in a first step, a combined immunological detection or selection is effected. There is understood by antibody derivative in this application any type of altered antibody or antibody fragment which has a binding site, for example single-chain antibodies, antibody fragments, such as FAB fragments or recombinant antibodies. When "antibodies" are mentioned in the following, antibodies and/or antibody derivatives are always denoted.

In a second step, at least one marker is then detected on a molecular-biological basis with a predefined combination of detection reagents, said marker being specific for the sought cells or being able to be found preferentially in the latter so that here again the sought cells are selected specifically. This therefore concerns here a combined molecular-biological detection. The basic concept of the present invention is therefore to combine a detection via a combination of immunological parameters with a detection via a combination of molecular-biological parameters. Surprisingly, quite exceptional detection results are produced as a result, with which an advance is made into areas of detection which were not accessible previously to all the known techniques from the state of the art. Therefore concentrations of sought cells in blood samples down to two cells per 5 milliliters can even be detected. A specificity and sensitivity of this type has not been achieved previously in the state of the art.

Eukariotic cells carry a multiplicity of different molecules on their cell surface. Corresponding to the origin and the function of the individual cell, the combination of the expressed surface molecules differs so that cell type-specific patterns are produced. Antibodies are used to detect these cell type-specific patterns. Antibodies bind with high specificity to their antigen, here to selected surface molecules. This property is used in order to recognise cells by means of specific antibody binding by means of their cell type-specific patterns and to distinguish them from each other.

For example the expression of special surface proteins of tumour cells differs from non-transformed cells of this cell type.

A selection of the target cells precedes the detection of the markers via the binding of various antibodies to the sought cells. Because the expression of special surface proteins differentiates cells of one type from cells of another type. Thus for example the expression of special surface proteins differentiates tumour cells from non-transformed cells of this cell type.

Since the special pattern of the surface antigens for example in the case of tumour cells also differs from blood cell-typical patterns, tumour cells in the blood can be differentiated. In order to identify tumour cells, antibodies which specifically recognise these special surface proteins are used as tools. The specific antibody binding is exploited for various analysis and separation methods.

Due to the intensive binding of immunoglobulins, selected specially for this purpose, separation of the detected cells from non-detected cells is possible in addition to detection of cells via their surface epitope.

Various separation principles are possible:

1. Separation Principle Based on Liquid Phase; e.g. Flow Cytometry:

For the flow-cytometric analysis, antibodies are coupled with fluorescence colorants. Isolated cells are conducted past a light source (laser) individually in a constant liquid flow. Upon illumination of the cells, the fluorescence colorants bound to the antibodies are excited and radiate light of specific wavelengths. The radiated light is detected and the measured signal is stored in a digital form. The light signal can be assigned to individual cells. The antibody-marked cell is detected thus and can now be separated from other cells. For separation the cells are isolated into the smallest drops. After detection of the antibody-marked cell, the corresponding drop is directed into a collection receptacle. A concentration of this type can be effected for example by FACS flow cytometry. For example concentrated cells with fluorescence-marked monoclonar antibodies against tumour-specific surface proteins are thereby incubated. The marked cells are washed twice with PBS and, subsequent thereto, $10^7$ cells are resuspended in 1 ml PBS. For the isolation of the tumour cells, a FACS vantage SE flow cytometer (Becton Dickinson) is used. Data recording, instrument control and data evaluation are effected via the CellQuest programme. The sorted cells are transferred into a 1.5 ml reaction vessel (filled with 1 ml PBS). The RNA can then be isolated as described later.

2. Separation Principle Based on Solid Phase; e.g. Magnetic Separation:

Antibodies are coupled to pseudo-magnetic particles for the magnetic separation. After introduction of the pseudo-magnetic particles into a magnetic field, the particles migrate in the magnetic field. During the movement in this magnetic field, cells to which these coupled antibodies are bound, are entrained and separated from other cells.

For cell detection by means of magnetic particles, antibodies are thus coupled to pseudo-magnetic particles which have a defined number of chemically activated sites on their surface. Coupling methods are known for example from James P. Gosling, Solid-phase Concepts and Design, in: R. F. Masseyeff, W. H. Albert N. A. Staines (eds), Methods of Immunological Analysis, Vol. 1, VCH Verlagsgesellschaft mbH, Weinheim, pp. 507-529. The specificity of the separation is determined via the specificity of the antibodies. A blood sample containing target cells is mixed with antibody-coupled magnetic particles; then particles and blood are moved relative to each other, for example by "overhead rotation" of samples situated in a closed container or by movement of the particles due to changing magnetic fields. Those target cells which are detected by an antibody bound to the solid phase and hence securely bound, follow the movement of the particles. It is possible as a result, when applying a magnetic field, to withdraw the particles with the cells bound thereon from the blood (e.g. onto the wall of the separation vessel). The blood which is target cell-depleted in this manner can be exchanged for other solutions, the cells separated via magnetic particles remaining in situ until switching off/removal of the magnetic field and being available for further applications.

As an alternative to the represented separation principles, also any other separation principles from the state of the art, which are based on marking cells with antibodies, can be used.

According to the invention, specific antibody mixtures are used advantageously for the detection of the tumour cells. For example, a combination of the antibodies MOC-31 and Ber-EP4 is suitable for detecting tumour cells in the blood.

TABLE 1

| | Antibody mixture | |
|---|---|---|
| Antigen | Clone | Concentration |
| epith. rel. antigen | MOC-31 (Novocastra Co.) | 1.25 µl/$10^6$ cells |
| epithelial antigen | Ber-EP 4 (DAKO Co.) | 0.924 µg/$10^6$ cells |

By means of the antibody mixture in the preceding Table 1, tumour cells are detected preferentially, however with high specificity. This is based on the preferential expression of specific surface proteins which differentiates cancer cells from other cells.

Antibody mixtures of this type, in comparison to the respectively separately used antibodies in cell detection and cell separation, show increased sensitivity dependent upon the method which is applied.

The present invention is substantially based furthermore on the fact that cell markers in the blood of patients are detected not for instance at an immunological or enzymatic level but by the fact that a molecular-biological marker, for example mRNA (messenger ribonucleic acid) of sought cells in a sample, for example in a blood sample, is detected.

Since individual markers are expressed differently in a therapy-dependent manner, a combination of tumour markers is advantageously tested in order to detect all the tumour cells circulating in the blood. As a result, tumour cells can also be detected when the expression of a specific marker is relatively low in a patient or in an illness stage, which otherwise could lead to a putatively negative result. The use of markers comes up against limits however usually for the reason that mononuclear blood cells have a background expression ("illegitimate transcription") which impedes exact analysis.

The expression of the genes mentioned in Table 2 is detected as a marker, for example of tumours. The detection can thereby be implemented for one or two markers or also for any number of these tumour markers in combination with each other. The kit according to the invention can therefore contain two oligonucleotide pairs for one, two or any selection or for all of the tumour markers.

TABLE 2

| Gene or gene product | Gene | Alternative designation |
|---|---|---|
| Human carcinoma-associated antigen GA733-2 gene | GA733-2 | GA733.2 |
| Human epidermal growth factor receptor (EGFR) gene | EGFR | EGFR |
| Human carcinoembryonic antigen (CEA) gene | CEA | CEA |
| Homo sapiens mucin 1 (MUC1) | MUC1 | CA15-3 |
| Homo sapiens C-erb B2/neu protein (ERBB2) gene | HER-2/neu | HER-2 |
| Homo sapiens claudin 7 (CLDN7), mRNA | claudin7 (CLDN7) | Claudin-7 |
| Alkaline phosphatase, placenta-like (Nago isozyme), (Germ-cell alkaline phosphatase), (PLAP-like) | ALPPL2 (GCAP) | PLAP |
| Homo sapiens gastrin-releasing peptide receptor (GPPR) gene | GRPR | GRPR |
| Homo sapiens high-mobility group (nonhistone chromosomal) protein isoform I-C (HMGIC), mRNA | HMGIC | HMGI-C |
| Homo sapiens gene for cytokeratin 20 | CK20 | CK2O |
| Human MAGE-3 antigen (MAGE-3) gene | MAGE-3 | MAGE-3 |
| Homo sapiens stanniocalcin 1 (STC1) gene | stanniocalcin 1 (STC1) | stanniocalcin |

As a result, all those cases are rightly neglected in which the tumour markers are likewise expressed for example on the basis of other illnesses and only proceed into the bloodstream as a protein. Because of the first immunological selection step, only cells are consequently detected which, on the one hand, are themselves situated in the blood sample and, on the other hand, express the respective tumour marker or tumour markers. Consequently this thereby concerns tumour cells which stem from their original tumour tissue and were entrained in the blood of the patients. Since in the blood of a person who does not have a tumour, the mRNA of the tested markers is normally not expressed, a direct correlation is revealed between the occurrence of the associated mRNA and a metastasis already in the early stage in the metastasising process.

Not only the mRNA of a single tumour marker is thereby advantageously detected but a combination of markers is tested. It is possible as a result to be able to detect cancer forms via their cells metastasising in the blood. This means that, in the case of testicular tumours, both seminal and non-seminal testicular cancer forms or also mixed tumours with components of a seminoma and hence 90-95% of all malignant tumours of the testicle, namely all the germ cell tumours, are detected.

For the detection of testicular tumour cells, a combination of at least two of the following markers is hence proposed according to the invention:

GA733.2
GCAP/PLAP
HMGI-C
GRPR.

For the detection of breast cancer cells, a combination of at least two tumour markers of the following marker groups is proposed according to the invention:

a) EGFR, CEA, stanniocalcin, MAGE 3, CK20, claudin 7, Her-2/neu, MUC1 and GA 733.2;
b) CK20, MAGE 3 and MUC1
c) Her-2/neu and claudin7 and
d) EGFR, CEA and stanniocalcin For the detection of intestinal (colon) cancer cells, a combination of at least two tumour markers of the following marker groups is proposed according to the invention:

a) CK20, EGFR, GA 733.2, CEA and stanniocalcin
b) CK20, EGFR, CEA and stanniocalcin and
c) EGFR, CEA and 733.2

A few examples are given in the following from which it emerges that, with the method according to the invention, a detection sensitivity is achieved which goes far beyond anything known previously in the prior art. FIGS. 1 to 10 show the results of different test protocols.

The basic procedure is common to all examples, said procedure comprising a first step with immunological concentration of target cells and a second step of detection of mRNA markers in the immunologically concentrated cells. In the following, these steps are described in a general form in so far as they are identical for all the examples.

1. Immunological Concentration of the Target Cells from Peripheral Blood.

Firstly, a peripheral blood sample was taken and a defined number of target cells was added thereto, for example 2, 10, 100 cells of a specific tumour type.

Furthermore, antibodies were coupled to magnetic particles. As antibodies, the antibodies presented subsequently in Table 3 were thereby used.

TABLE 3

| Antigen | Clone | Company |
|---|---|---|
| Epithelial membrane antigen | GP1.4 | Novocastra |
| Epithelial antigen | MOC-31 | Novocastra |
| Epithelial antigen | Ber-EP4 | DAKO |
| Muc 1 | HMPV.2 | Pharmingen |
| PLAP | 8B6 | Cymbus Biotechnology LTD |
| Epithelial membrane antigen | E29 | DAKO |
| Epithelial membrane antigen | 131-11741 | HISS |

The magnetic particles were thereby used with a particle concentration of $4 \times 10^8$ beads/ml (CELLection™ Pan Mouse IgG Kit, Dynal Co.). The ratios between the antibody concentration and the antibodies coupled thereto are reproduced in Table 4.

TABLE 4

| Clone | Antibody concentration | μl Antibodies/ 25 μl particles |
|---|---|---|
| BerEP4 | 0.1 mg/ml | 4 μl |
| HMPV.2 | 0.5 mg/ml | 4 μl |
| MOC31 | k.A. dilution see manufacturer's instructions (lyophilisate) | 4 μl |
| GP1.4 | k.A. dilution see manufacturer's instructions (lyophilisate) | 4 μl |
| 8B6 | 0.1 mg/ml | 1 μl |
| 131-11741 | 0.5 mg/ml | 4 μl |
| E29 | 0.1 mg/ml | 4 μl |

The thus prepared magnetic particles were added to the blood according to the test batch and detection system. The corresponding addition of antibody-coupled magnetic particles per ml blood with an initial concentration of $4 \times 10^8$ beads/ml particles is reproduced in Table 5.

TABLE 5

| Tumor Antibody | Breast cancer diagnostic | Intestinal cancer diagnostic | Testicular cancer diagnostic |
|---|---|---|---|
| BeREP4 | 8.3 μl | 10 μl | 8 μl |
| HMPV.2 | 8.3 μl | | |
| MOC31 | | 10 μl | 8 μl |
| GP1.4 | 8.3 μl | | |
| 8B6 | | | 4 μl |

After a 2 hour incubation in the overhead shaker, the magnetic particles, which occurred possibly as cell antibody magnetic particle complexes, were washed, by means of a magnetic particle concentrator (MPC®-S, Dynal Co.), 3 times with PBS (phosphate buffer saline) and the adhering cells were subsequently treated corresponding to the subsequently described RNA isolation protocol.

As an alternative to separation by means of magnetic particles, it is possible to use an immunological separation by means of flow cytometry (fluorescence-associated cell sorting, FACS).

A first relative concentration of the tumour cells is achieved here by depletion of the erythrocytes. For this purpose, full blood (with EDTA) is mixed with a hypotonic erythrocyte lysis buffer and incubated for 30 minutes at room temperature. The remaining nuclei-containing cells are centrifuged and resuspended in PBS/BSA. The thus obtained cells are subsequently incubated with antibodies which are marked with a fluorophore. The target cells, which are marked in a fluorescing manner by means of binding to an antibody, were separated then via FACS.

As an alternative, it is possible to concentrate by density gradient centrifugation. By means of centrifugation of this type with different density gradients, cells of different average volume density are separated from each other. Mononuclear blood cells are separated by means of a Ficoll-Hypaque gradient (Pharmacia Co., Uppsala, Sweden) and subsequently are washed twice with PBS/1% FCS. Subsequently, a solid phase-coupled concentration (e.g. via magnetic particles) or a liquid phase-based separation (FACS) of the target cells is effected as described above.

2. mRNA Isolation

Firstly, isolation of the total RNA of the cells separated as described above is effected. This is effected with the QIAamp RNA blood Mini Kit (Qiagen Co., Hilden) according to the manufacturer's instructions there, the lysis buffer having been given directly to the cells bound to the magnetic particles. Due to an additional DNA digestion on the column, a contamination with genomic DNA is avoided. This DNA digestion is effected with the RNase-free DNase Set, Qiagen Co., Hilden.

Alternatively, also an mRNA isolation, e.g. by means of oligo(dT)-coupled magnetic particles, Dynabeads® mRNA™ Micro Kit, (Dynal Co.) can be effected. This isolation is also effected corresponding to the manufacturer's instructions indicated in the kit.

As a further alternative to RNA isolation, the isolated cells are lysed by addition of Trizol reagent (Gibco Co. BRL, NY, USA) and homogenised by means of a pipette. After subsequent chloroform extraction, the RNA-containing aqueous phase is precipitated in isopropanol at −80° C. After being washed twice and centrifuging in 80% ethanol, the pellet is dried in air and subsequently is resuspended in RNase-free water. This reprocessing step is likewise effected according to conventional protocols.

3. Reverse Transcription

A reverse transcription, in which the mRNA is transcribed into cDNA follows the isolation of the RNA.

In addition, the RNA is denatured in a corresponding volume of water according to the reaction batch in Table 6 together with oligo(dT) 15 primers (Promega Co., Mannheim) for 5 minutes at 65° C. and subsequently is incubated directly on ice.

TABLE 6

Components of the cDNA synthesis
The cDNA synthesis is effected in a 20 μl reaction batch

| Components | Volumes | End concentration |
|---|---|---|
| RNA/mRNA | 10 μl | — |
| 10x RT buffer | 2 μl | 1x |
| DNTP mix (per 5 mM) | 2 μl | respectively 0.5 mM |
| Oligo(dT) primer (10 μM) | 2 μl | 1 μM |
| RNase inhibitor | 1 μl | 0.5 units/μl |
| Reverse transcriptase | 1 μl | 4 U |
| RNase-free water | up to 20 μl | |

The cDNA synthesis is effected at 37° C. for one hour with subsequent inactivation of the reverse transcriptase by heating for 5 minutes at 95° C. and subsequent cooling on ice. For this purpose, a Sensiscript Reverse Transcriptase Kit, Qiagen Co., Hilden was used according to the protocols indicated there.

When already using oligo(dT)-coupled magnetic particles for isolating mRNA, the addition of oligo(dT) primers is omitted, i.e. the oligo(dT)-linker serves simultaneously as primer for the reverse transcription, the magnetic particles remaining here in the batch.

4. PCR

Subsequent to the transcription of mRNA into cDNA, a polymerase chain reaction (PCR) is effected with β-actin as internal control.

The oligonucleotides cited in Table 7 were used as PCR primer for amplification of cDNA corresponding to different marker genes, as are indicated in the first column.

TABLE 7

List of PCR primers

| Primer name | Sequence 5'→3' | PCR product |
|---|---|---|
| Tumour markers | | |
| GA733.2 sense | AATCGTCAATGCCAGTGTACTTCA | 395 bp |
| GA733.2 sense | TAACGCGTTGTGATCTCCTTCTGA | |
| EGFR sense | AGTCGGGCTCTGGAGGAAAAGAAA | 163 bp |
| EGFR antisense | GATCATAATTCCTCTGCACATAGG | |
| CEA sense | AGAAATGACGCAAGAGCCTATGTA | 231 bp |
| CEA antisense | AACTTGTGTGTGTTGCTGCGGTAT | |
| CA 15-3 sense | TCAGCTTCTACTCTGGTGCACAAC | 299 bp |
| CA-15-3 antisense | TGGTAGTAGTCGGTGCTGGGATCT | |
| Her-2 sense | CCCAGTGTGTCAACTGCAGCCAGT | 265 bp |
| Her-2 antisense | CAGATGGGCATGTAGGAGAGGTCA | |
| claudin-7 sense | GTCTTGCCGCCTTGGTAGCTTGCT | 225 bp |
| claudin-7 antisense | TGGACTTAGGGTAAGAGCGGGGTG | |
| GCAP/PLAP sense | GCCACGCAGCTCATCTCCAACATG | 440 bp |
| GCAP/PLAP antisense | ATGATCGTCTCAGTCAGTGCCCGG | |
| GRPR sense | TCTCCCCGTGAACGATGACTGGTC | 308 bp |
| GRPR antisense | TGAAGACAGACACCCCAACAGAGG | |
| HMGI-C sense | AAAGGCAGCAAAAACAAGAGTCCC | 213 bp |
| HMGI-C antisense | CCAACTGCTGCTGAGGTAGAAATC | |
| CK20 sense | ATCTCCAAGGCCTGAATAAGGTCT | 336 |
| CK20 antisense | CCTCAGTTCCTTTTAATTCTTCAGT | |
| MAGE3 sense | CTCCAGCCTCCCCACTACCATGAA | 375 bp |
| MAGE3 antisense | TTGTCACCCAGCAGGCCATCGTAG | |
| stanniocalcin sense | AACCCATGAGGCGGAGCAGAATGA | 254 bp |
| stanniocalcin antisense | CGTTGGCGATGCATTTTAAGCTCT | |
| Internal control | | |
| actin sense | CTGGAGAAGAGCTACGAGCTGCCT | 111 bp |
| actin antisense | ACAGGACTCCATGCCCAGGAAGGA | |

Table 7 contains in the first column the data about the tumour marker to be detected, two oligonucleotides respectively (sense and antisense) being indicated as primer pair. The length of the PCR product, which is produced by the primers indicated in column two, is indicated in column three. The PCR was implemented with the batch indicated in Table 8.

TABLE 8

PCR batch
The PCR synthesis was effected in a 50 μl reaction batch

| Components | Volumes | End concentration |
|---|---|---|
| cDNA | 6 μl | |
| 10x PCR buffer* | 5 μl | 1x |
| dNTP mix | 1 μl | respectively 200 μM |
| primer | see Tables 7 and 9 | |
| Taq-DNA polymerase** | 0.5 μl | 2.5 U |
| [Q-solution***] | 10 μl] | |
| H₂0 | up to 50 μl | |

(* contains 15 mM MgCl₂;
**HotStarTaq ™ DANN Polymerase; Qiagen, Hilden)
(***The addition of 10 μl Q-solution (Qiagen, Hilden) is only necessary for detecting GCAP/PLAP)

Table 9 indicates a list of the specific primer combination and primer concentrations as end concentration in the PCR batch. In the following examples for the various tumour types, breast cancer, intestinal cancer and testicular cancer respectively, a mulitplex combination for these primers is shown by way of example, as is indicated in Table 9.

TABLE 9

List of the specific primer combinations and primer concentration (end concentration in the PCR batch)

| Marker Primer | Breast cancer-1 | Intestinal cancer-1 | Testicular cancer-1 |
|---|---|---|---|
| GA733.2 sense | 500 nM | 500 nM | 500 nM |
| GA733.2 antisense | 500 nM | 500 nM | 500 nM |
| EGFR sense | | 750 nM | |
| EGFR antisense | | 750 nM | |
| CEA sense | | 750 nM | |
| CEA antisense | | 750 nM | |
| CA15-3 sense | 400 nM | | |
| CA15-3 antisense | 400 nM | | |
| Her-2 sense | 300 nM | | |
| Her-2 antisense | 300 nM | | |
| claudin-7 sense | 400 nM | | |
| claudin-7 antisense | 400 nM | | |
| GCAP/PLAP sense | | | 800 nM |

TABLE 9-continued

List of the specific primer combinations and primer
concentration (end concentration in the PCR batch)

| Marker Primer | Breast cancer-1 | Intestinal cancer-1 | Testicular cancer-1 |
|---|---|---|---|
| GCAP/PLAP antisense | | | 800 nM |
| GRPR sense | | | 500 nM |
| GRPR antisense | | | 500 nM |
| HMGI-C sense | | | 500 nM |
| HMGI-C antisense | | | 500 nM |
| β-actin sense | 100 nM | 200 nM | 100 nM |
| β-actin antisense | 100 nM | 200 nM | 100 nM |

The PCR conditions (cycle number, cycle process etc.) are given in Tables 10 and 11.

TABLE 10

PCR conditions

| | | |
|---|---|---|
| Initial denaturation | 95° C. | 15 min |
| Cycle | | |
| 1. denaturation | 94° C. | 1 min |
| 2. annealing | x° C. | 1 min (see Table 11) |
| 3. extension | 72° C. | 1 min |
| Final extension | 72° C. | 10 min |
| | 4° C. | pause |

TABLE 11

Multiplex-specific annealing temperature and cycle number

| Marker | Breast cancer-1 | Intestinal cancer-1 | Testicular cancer-1 |
|---|---|---|---|
| Annealing temperature | 60° C. | 58° C. | 58° C. |
| Cycle number | 35 | 40 | 40 |

(Thermocycler: PCT 200; Biozym)

The thus produced amplificates of the cDNA were separated electrophoretically by means of a bioanalyser 2100 (Agilent Co.). For this purpose, 1 µl of the PCR product was separated in the bioanalyser on a DNA chip (500) and the separation result was documented electronically. FIGS. 1-10 were produced in this manner.

Alternatively, 25 µl of the PCR product are separated via a 2.5% agarose gel and the DNA bands are coloured with ethidium bromide. The documentation is effected for example by means of the DUO Store System of the Intas Co.

Alternatively, a fragment analysis can furthermore by implemented for example by means of an ABI prism 310 genetic analyser (PE Applied Biosystem Company, Weiterstadt). For this purpose, 1 µl of the PCR product is then used in the dilution 1:50. In this case, fluorescence-marked primers are used.

FIG. 1 now shows the result of a method according to the invention for the detection of breast cancer cells in the blood. For this purpose, a defined quantity of tumour cells of a breast cancer cell line was added to the blood of healthy persons. The added cell number thereby was 10 cells (10 c) or 100 cells (100 c) per milliliter blood. FIG. 1A and 1B now show respectively electrophoretic separations, the individual bands being numbered with the same terms here and in the following. The term conductor designates calibrators of 50-600 bp length, a control is designated with RT-Ko which contained no mRNA, a control measurement is designated with PCR-Ko which contained no cDNA before the PCR. By "blood", there is designated the blood sample without inoculated tumour cells, by 10 c, the blood sample with 10 inoculated tumour cells per milliliter and by 100 c, the blood sample with 100 inoculated tumour cells per milliliter or per 5 milliliters. By "cell line", a control measurement with a large cell number of the tumour cell line in the sample is designated.

Results are presented in FIG. 1 when the selection was implemented in the first step with only one, two or all three of the following antibodies HMPV.2, GP1.4 and Ber-Ep 4. It can be detected immediately that when using only one antibody the detection of the tumour marker CA 15.3 (Mucd) is only low. The best results are achieved when two of the antibodies, namely HMPV.2 and Ber-Ep 4 or GP1.4 and Ber-Ep 4 are used for detection. The combination of all three antibodies, as can be detected by the intensity of the bands for the tumour marker CA 15.3, is already more effective. Hence it is established that, with a suitable selection of a specific number of specific antibodies, a significantly improved result is possible when detecting tumour cells. It is revealed also in particular that the simple conclusion that, when using a plurality of antibodies, the sensitivity would necessarily increase, is not possible. The opposite is possibly the case since a non-specific reaction with an increasing number of antibodies is more possible. It is therefore of particular importance to determine a suitable combination of antibodies experimentally.

Figure 2:
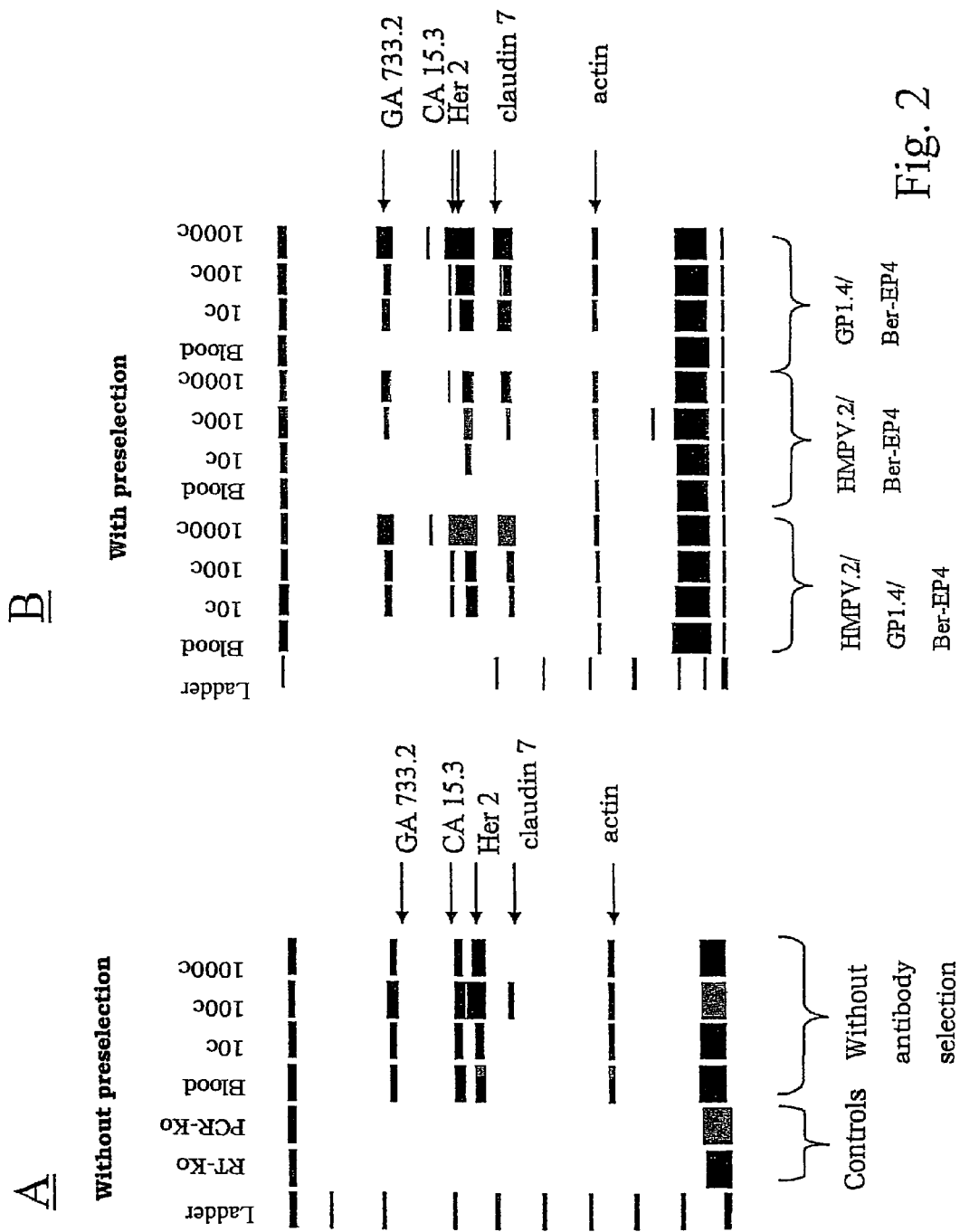

FIG. 2 now shows results of detection methods, in which, in FIG. 2A, no preselection by means of antibody marking was implemented and, in FIG. 2B, a preselection by means of antibody marking was implemented. In FIG. 2, combinations of the antibodies HMPV.2, Ber-Ep 4 and GP 1.4 have thereby been determined as a combination of two or of all three antibodies. At the same time, a multiplex determination of in total four markers, namely GA 733.2, CA 15.3, Her 2/neu and also claudin 7, was implemented. Here also, again 10, 100 or 1000 tumour cells of a breast cancer cell line were inoculated in blood and subsequently detected. It is shown here that without antibody selection a background expression for some of the mRNA markers (GA 733.2, CA 15.3 and Her 2/neu) is detected. A background of this type can be avoided when using each of the antibody combinations presented in FIG. 2B for preselection of the cells to be tested for mRNA. It is of interest again in FIG. 2B that the use of three antibodies is not definitely superior to the use of two antibodies, e.g. GP 1.4 with Ber-Ep 4. The selection of specific antibody combinations and also the selection of specific mRNA markers does however make it possible to detect the corresponding sought tumour cells down to 10 cells per milliliter blood without any non-specific background. The background expression was able to be eliminated and the sensitivity was significantly increased (see band for claudin 7).

Figure 3:
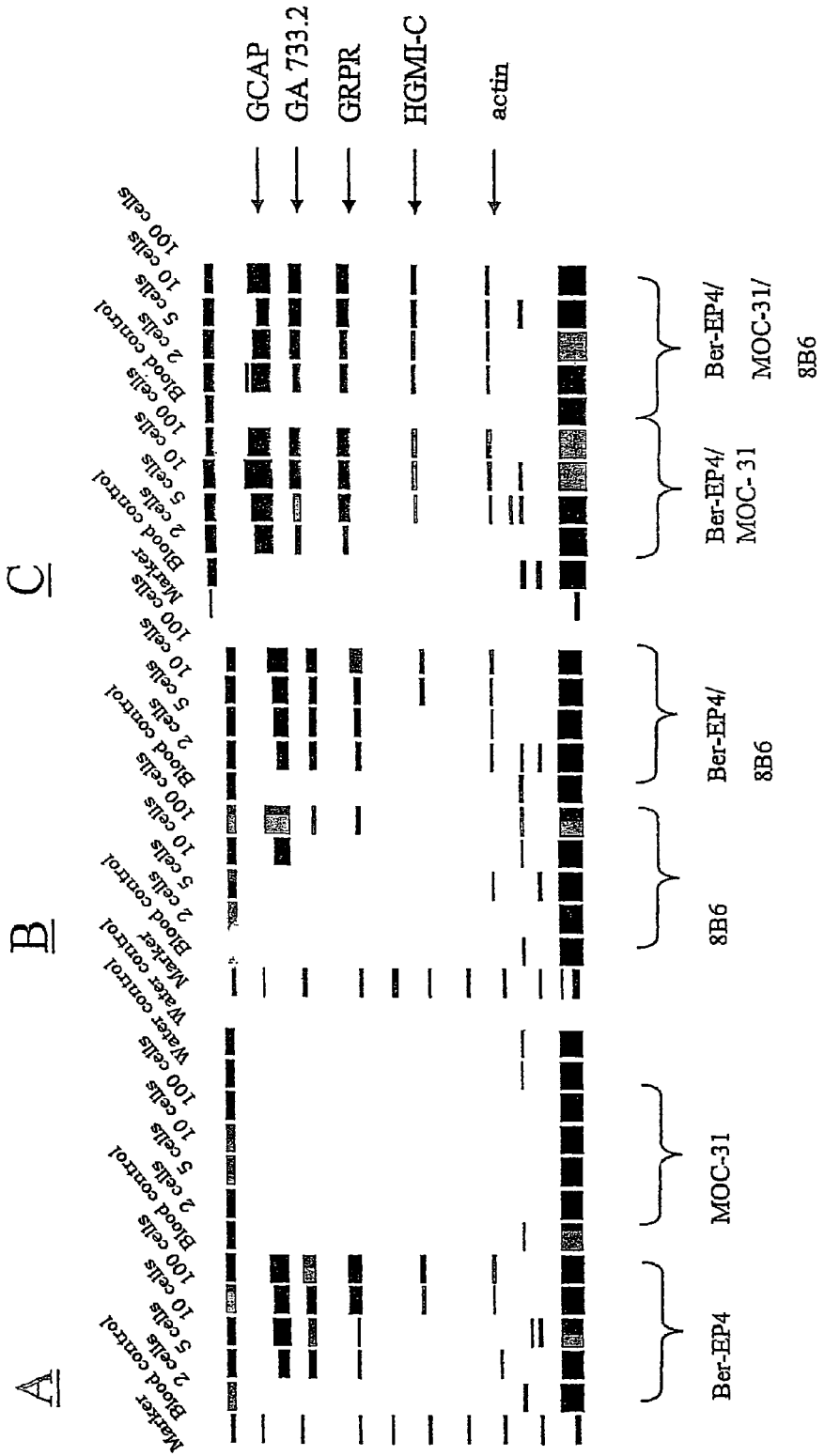

In FIG. 3, the result of a method according to the invention with tumour cells from a testicular cancer cell line inoculated in blood is presented. Again, all the tumour cells are selected from the blood sample which are marked by one of the presented antibodies. Subsequently, testing is implemented for in total four mRNA markers (GCAP, GA 733.2, GRPR and HGMI-C). It is shown here that, when using only one antibody, such as Ber-Ep 4, only down to 10 cells per milliliter blood are detected by means of the marker HGMI-C and, when using the antibody MOC-31, absolutely no testicular cancer cells are detected. The same applies for the antibody 8B6 which has only a low sensitivity.

The combination of the antibodies Ber-Ep 4 and 8B6 likewise leads to a deficient detection by means of the marker HGMI-C and also the combination of the antibodies Ber-Ep 4 and MOC-31. An optimal detection result for all of the four tested markers is produced for testicular tumour cells when using in total three antibodies Ber-Ep 4, MOC-31 and 8B6, where down to 2 cells per milliliter blood are detected reliably via each individual one of the markers. If two markers are detected according to the invention with the two detection reactions, a more reliable detection of -a minimal cell number with simultaneous avoidance of background detection can be implemented when selecting two markers from the markers used for FIG. 3.

Figure 4:
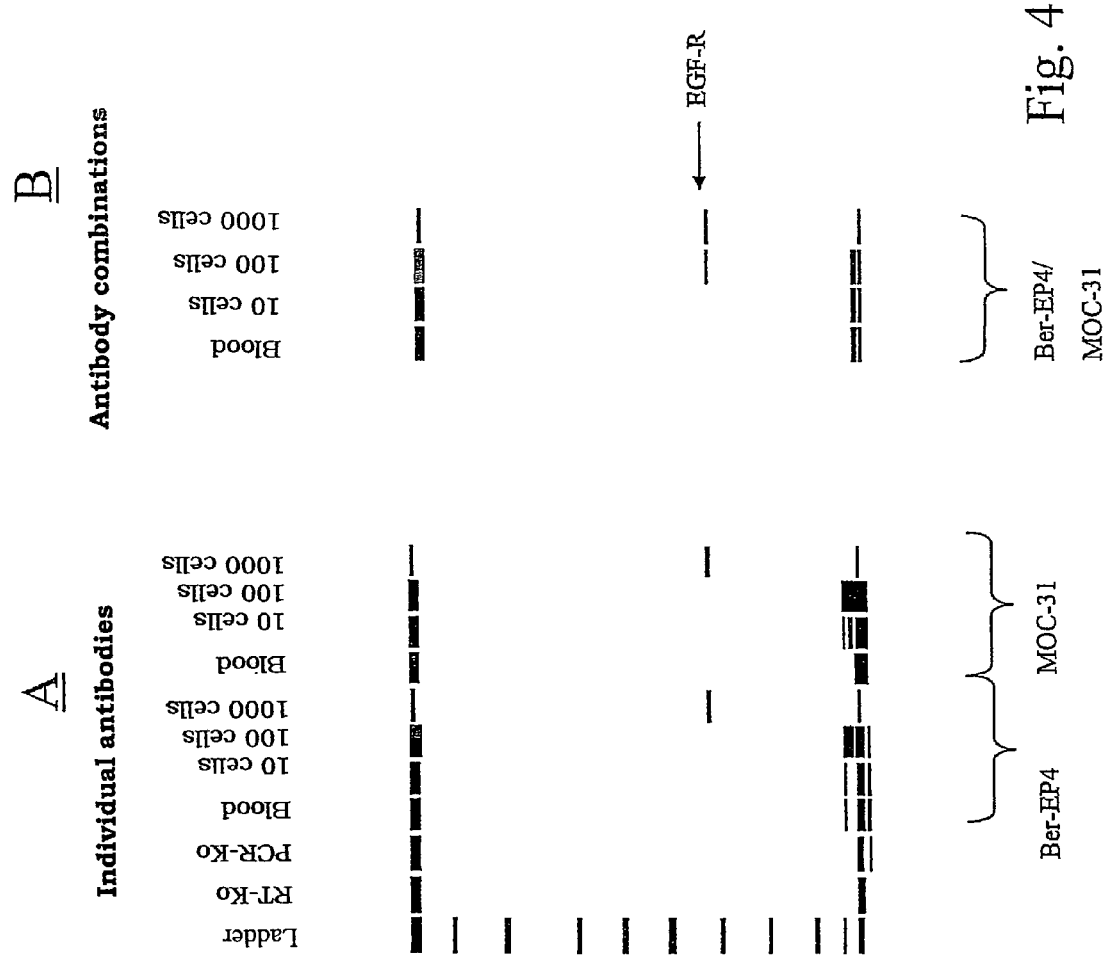

FIG. 4 shows the detection of intestinal cancer cells which were inoculated in the blood of a healthy person. It is shown here immediately that the use of a combination of the antibodies Ber-Ep 4 and MOC-31 leads to an improved sensitivity with respect to the mRNA marker EGF-R. When using the two antibodies at the same time, a detection sensitivity of 100 cells per milliliter blood is achieved whilst, when using only one antibody, the sensitivity is approximately 1000 cells per milliliter blood.

Figure 5:
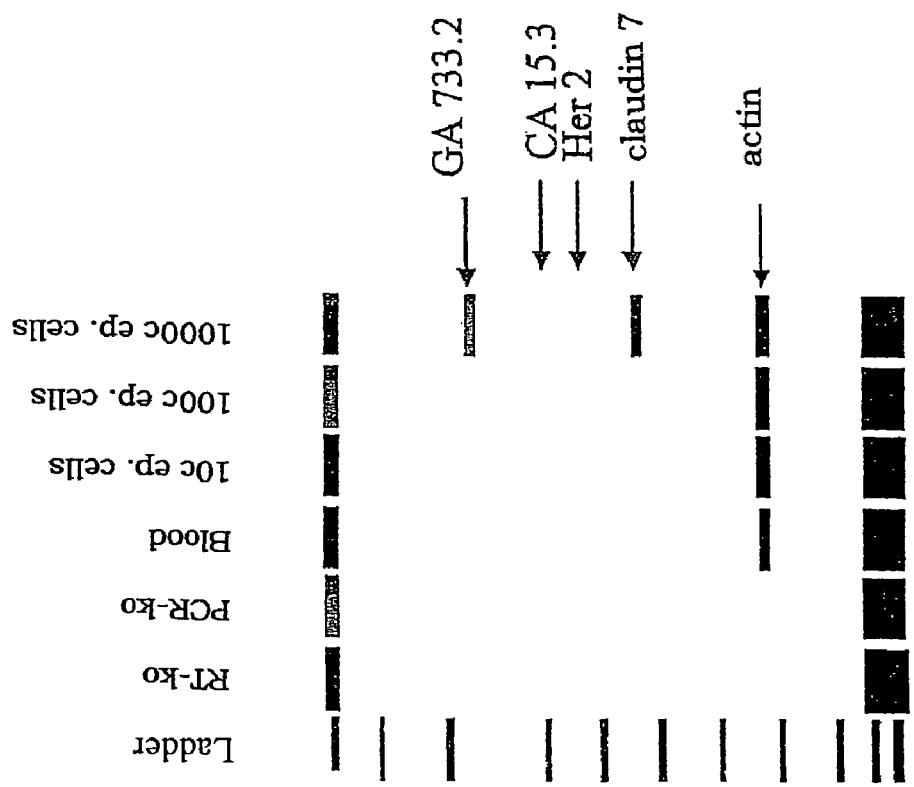

FIG. 5 shows a test in which, by means of an antibody combination of Ber-Ep 4, HMPV.2 and GP1.4, the cells marked with at least one of the antibodies were selected and subsequently were tested for the mRNA markers GA 733.2, CA 15.3, Her 2 and claudin 7. Admittedly, no tumour cell was added here to the blood of the healthy persons but defined quantities of epithelial cells were. As emerges immediately from FIG. 5, only two of the markers show a positive result in the case of a very high number of epithelial cells.

Figure 6:
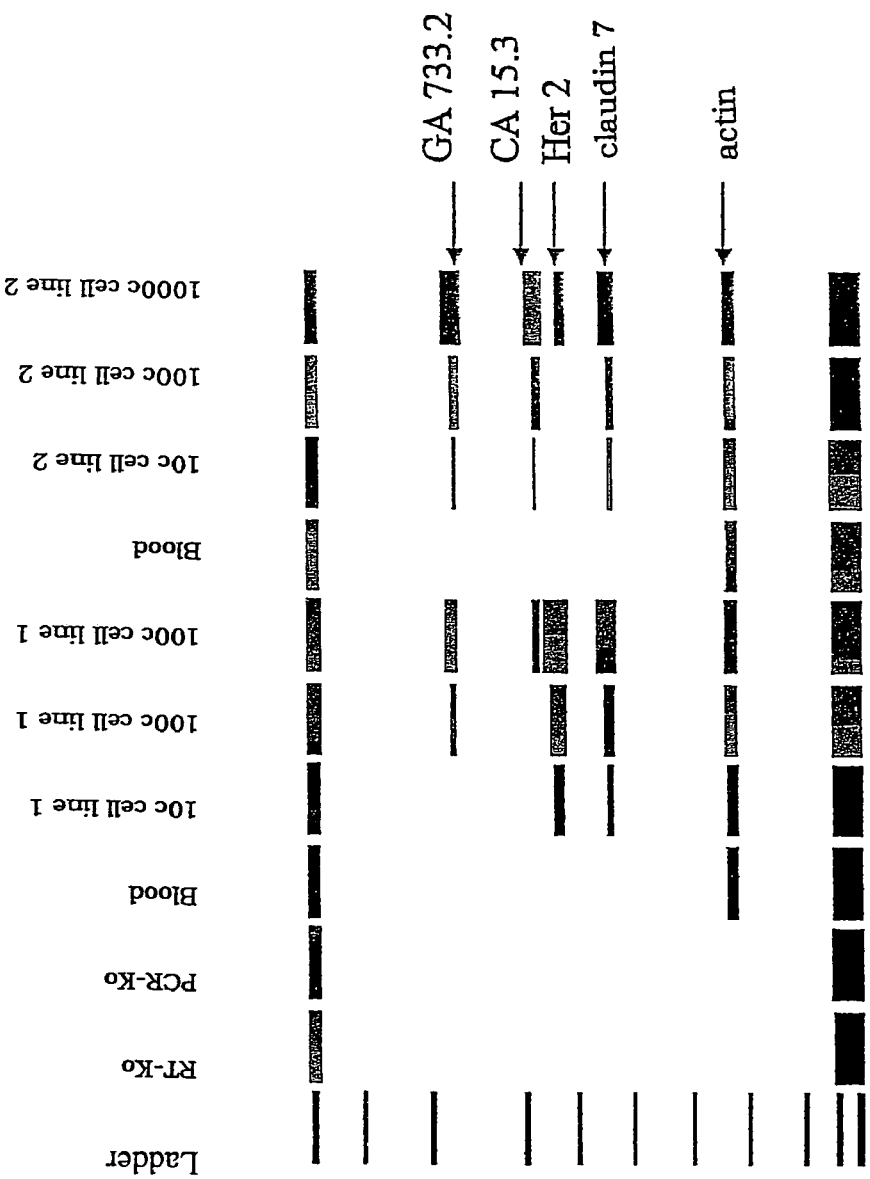

In FIG. 6, tumour cells of two different breast cancer cell lines (MCF-7 and SKBR-3) were added to a blood sample. The antibodies Ber-Ep 4, HMPV.2 and GP1.4 were used in combination as antibodies. As can be detected immediately, a detection of breast cancer cells by using the four mRNA markers GA 733.2, CA 15.3, Her 2 and claudin 7 respectively is ensured with certainty down to 10 cells of the individual cell lines per milliliter. A non-specific reaction in blood without breast cancer cells did not occur. Admittedly, the tumour markers GA 733.2 and CA 15.3 for the cell line 2 (SKBR-3) are more sensitive, whilst the tumour marker Her 2 for the cell line 1 (MCF-7) is more sensitive. Thus the individual subtypes of breasts cancer cells can then also be differentiated from each other by means of the occurring marker pattern.

Figure 7:
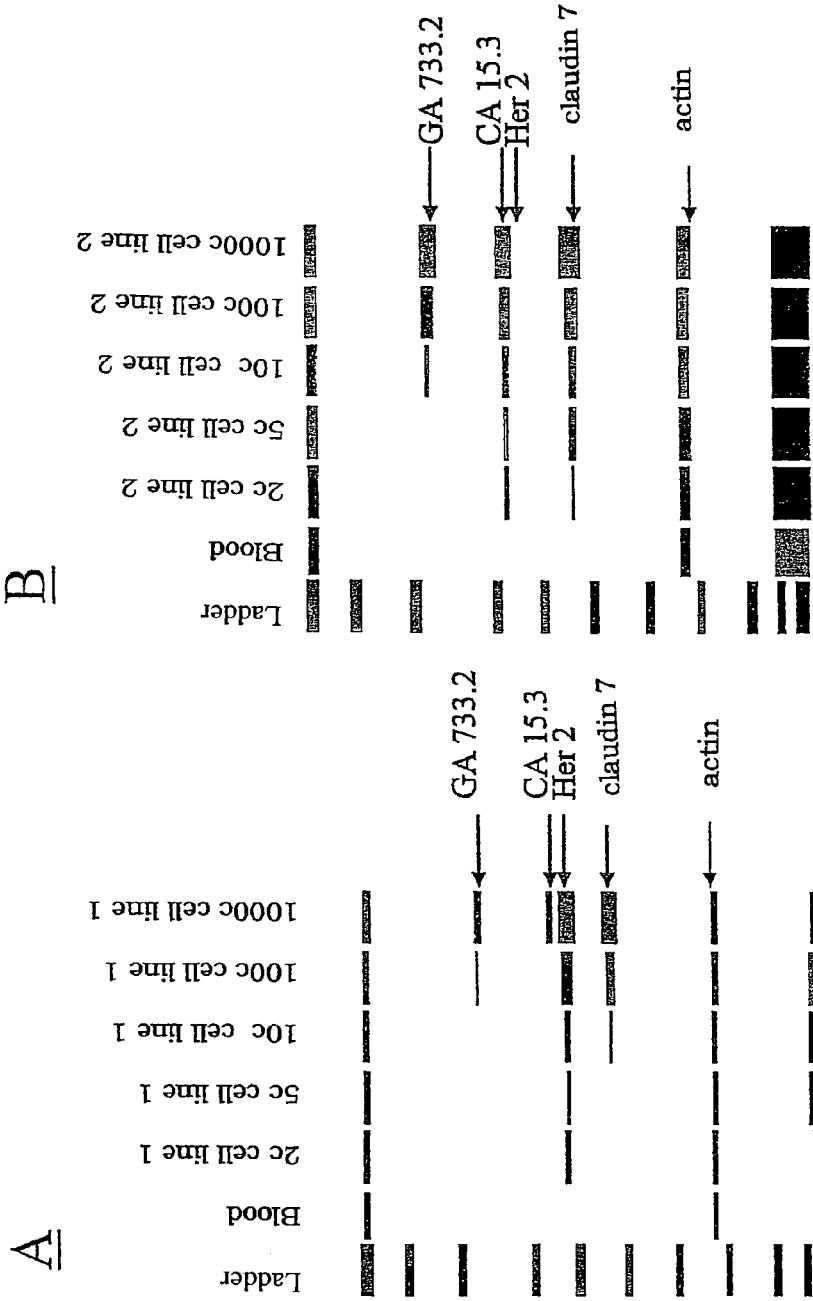

Also in FIG. 7, breast cancer cells of different cell lines have been inoculated in blood, (MCF-7) in FIG. 7A and SKBR 3 in FIG. 7B. As antibodies for selecting the cells from the blood sample, the antibodies Ber-Ep 4, HMPV.2 and GP1.4 were used in combination. It can be detected immediately that, when using a combination of mRNA markers GA 733.2, CA 15.3, Her 2 and claudin 7, in each case at least one of the markers reacts positively down to 2 cells per 5 milliliters of blood without tumour cells delivering an expression background. Here also, again a differential response behaviour of the two cell lines to the four different mRNA markers can be detected.

However, if both cell lines are located for example in one blood sample, then a detection of both cell lines would be ensured due to the selected marker combination in each case down to two cells per 5 milliliters blood, i.e. the detection of breast cancer cells in the blood would be possible with high sensitivity independently of the cell type of the breast cancer cell line.

Figure 8:
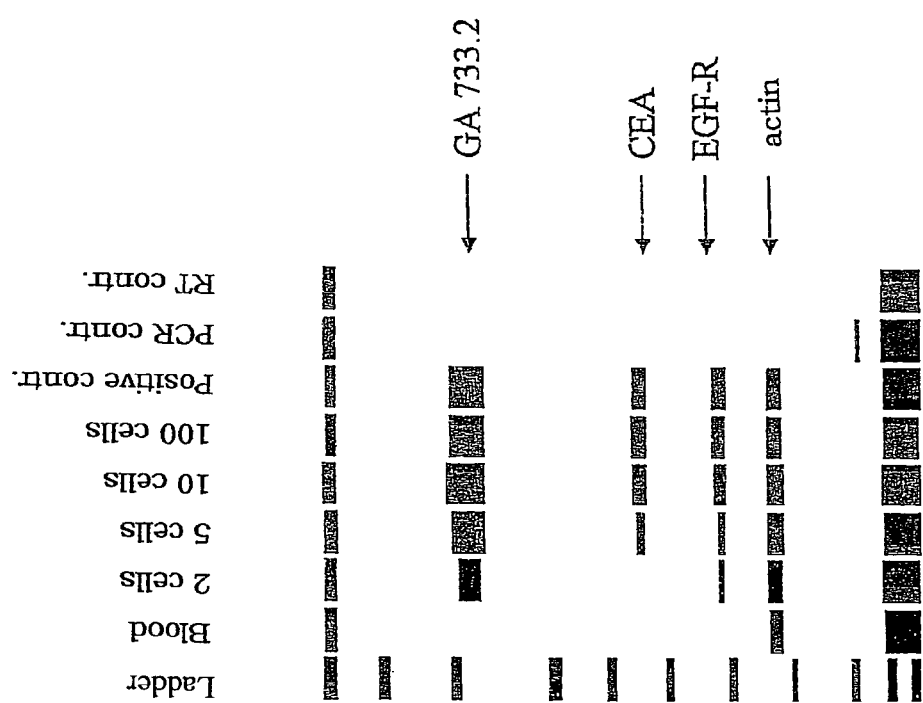

FIG. 8 shows the detection of intestinal cancer cells which were inoculated in blood. The selection of the cells was thereby effected with the two antibodies Ber-Ep 4 and MOC-31. The molecular-biological detection step was effected with the mRNA markers GA 733.2, CEA and EGF-R. Two tumour-cells were detectable in 5 milliliters blood.

Figure 9:
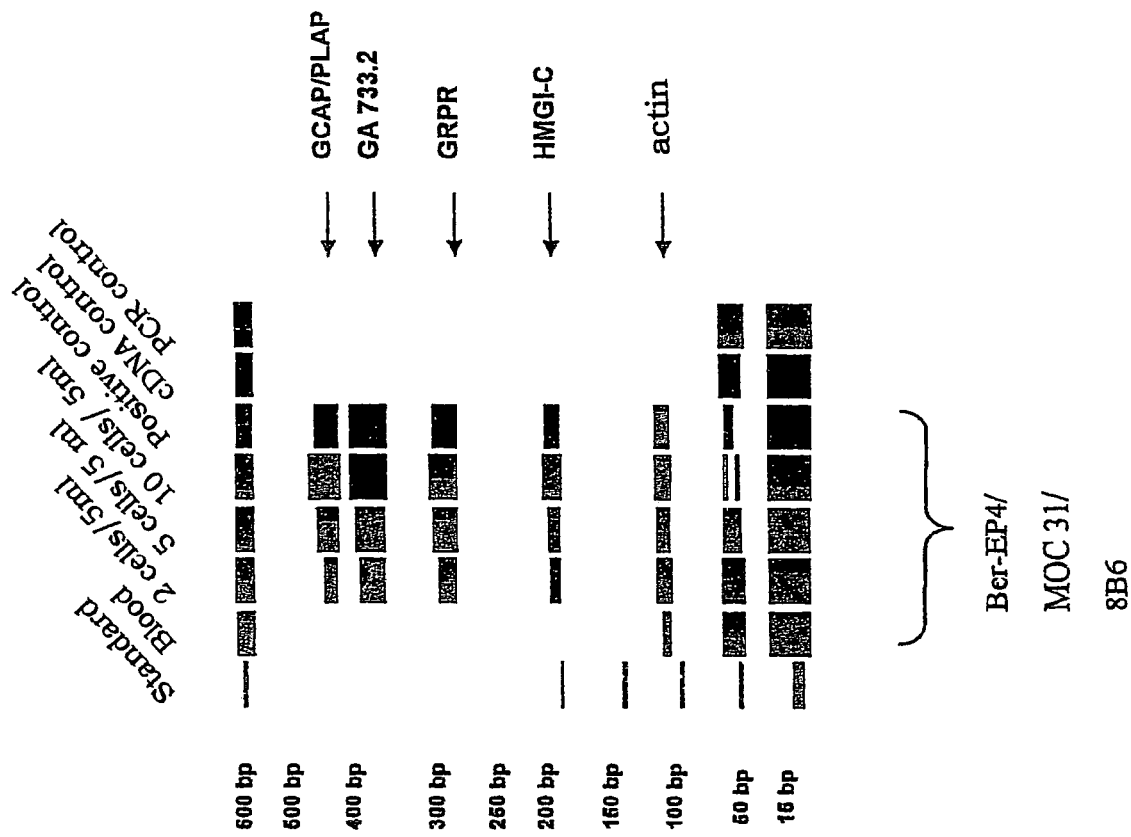

FIG. 9 shows in turn a measurement with a combination of three antibodies Ber-Ep 4, MOC-31 and 8B6 and also the mRNA markers GCAP/PLAP, GA 733.2, GRPR and HMGI-C in blood in which testicular cancer cells were inoculated.

With each of the molecular-biological markers, the detection down to two cells per 5 milliliters is successful when using this triple combination of antibodies for the cell selection in the immunological selection step.

Figure 10:
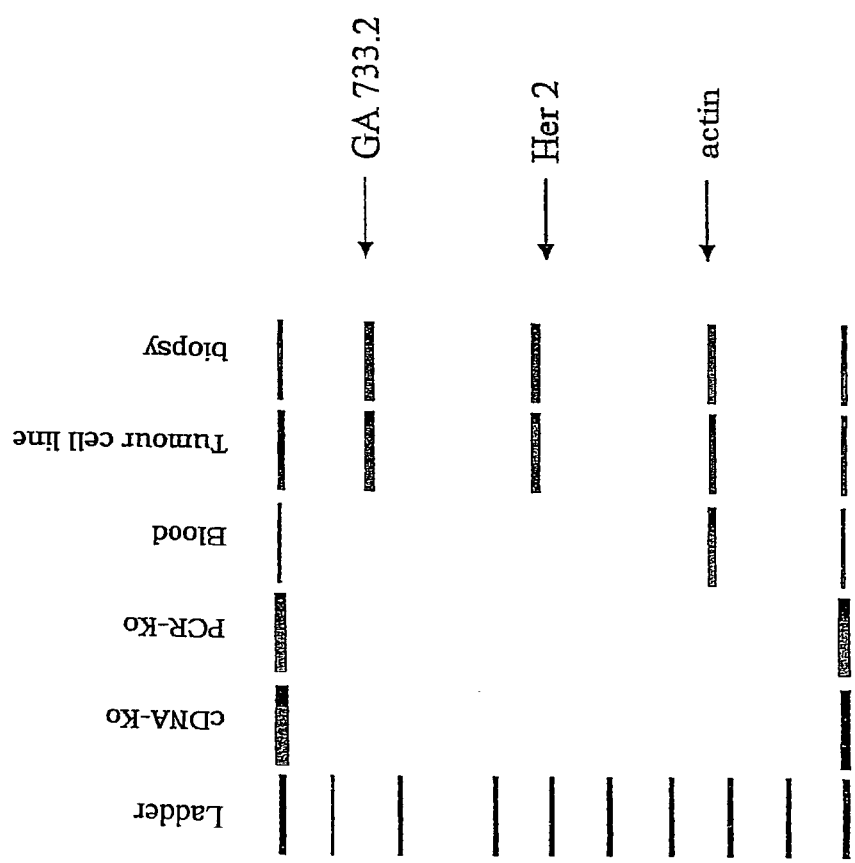

FIG. 10 shows finally the separation of uncommon cells from the cell mixture of a biopsy material. For this purpose, biopsy material from breast tissue, which contained tumour tissue with a suspected primary tumour, was isolated mechanically and separated via gauze from cell remnants, connective tissue etc. The obtained cell mixture, which contained both cells of the suspected tumour tissue and also cells of the surrounding healthy tissue, was mixed with a cell selection with an antibody mixture coupled to a solid phase (magnetic particles with antibodies GP1.4, HMPV.2 and Ber-Ep 4) and magnetically separated after incubation in order to produce the antigen-antibody binding. Subsequently, an mRNA detection was effected with reference to the markers GA 733.2 and Her 2. As a control, a cell line of a breast cancer was likewise determined in parallel at the same time. As can be detected, a positive detection is produced that the biopsy indeed contained a breast cancer tumour.

The bands, which are characterised in FIGS. 8 and 9 with "positive control", show results of samples with the cell lines HT 29 for intestinal tumour (FIG. 8) or Tera/1 for testicular tumour (FIG. 9).

The invention claimed is:

1. A method for detection of a predetermined biological cell in a sample containing biological cells comprising:
 (i) mixing the sample with (a) a predetermined combination of at least two antibodies and/or antibody derivatives that bind to two different epitopes of the cell to be detected, or with (b) at least one bispecific antibody and/or antibody derivative that binds to two different epitopes of the cell to be detected, wherein said predetermined combination of at least two antibodies or bispecific antibody provides an increased sensitivity in terms of the number of cells that can be detected in a given sample volume as compared to the number of cells that can be detected in said sample volume using a single monospecific antibody that binds to one of said epitopes,
 (ii) binding the cell with at least one of the antibodies and/or antibody derivatives thereby marking the cell,
 (iii) separating the marked cell from the sample, and
 (iv) testing the separated cell for the expression of a predetermined combination of at least two mRNAs, the expression of which is effected in the cell to be detected, wherein the expression of at least one of the mRNAs indicates the predetermined cell is detected,
wherein said increased sensitivity is achieved without a decrease in specificity.

2. The method according to claim 1, wherein the separation of the marked cell is effected in liquid phase.

3. The method according to claim 1, wherein antibodies or antibody derivatives coupled to solid phases are used in order to separate the marked cell from the sample.

4. The method according to claim 1, wherein the antibodies or antibody derivatives are marked with fluorophores, and the separation of the marked cell from the sample is effected by means of fluorescence-activated cell sorting.

5. The method according to claim 1, further comprising coupling the antibodies or antibody derivatives to magnetic particles to produce magnetic antibody-coupled particles, and magnetically separating the magnetic antibody-coupled particles from the sample after mixing with the sample.

6. The method according to claim 1, wherein the antibodies or antibody derivatives have binding sites which bind to tumor cells.

7. The method according to claim 1, wherein the antibodies or antibody derivatives have binding sites which bind to cells of one or more specific tumor types or sub-types.

8. The method according to claim 1, wherein the antibodies or antibody derivatives comprise binding sites which bind to epitopes of an epithelial antigen, an epithelial membrane antigen, the antigen MUC1 and/or the antigen PLAP.

9. The method according to claim 1, wherein at least one of the antibodies is selected from the group of antibodies consisting of GP1.4, MOC-31, Ber-EP 4, HMPV.2, 8B6, E29 and 131-11741.

10. The method according to claim 1, wherein the combination of antibodies comprises Ber-EP 4 and MOC31 or comprises at least two antibodies selected from the group of antibodies consisting of HMPV.2, GP1.4 and Ber-EP 4.

11. The method according to claim 1, wherein the combination of antibodies comprises at least two antibodies selected from the group of antibodies consisting of 131-11741, GP1.4, E29 and HMPV.2, or comprises at least two antibodies selected from the group of antibodies consisting of HMPV.2, GP1.4 and Ber-EP 4, whereby breast tumor cells are detected in the sample.

12. The method according to claim 1, wherein the combination of antibodies comprises the antibodies Ber-EP 4 and MOC-31, whereby colon tumor cells are detected in the sample.

13. The method according to claim 1, wherein the combination of antibodies comprises at least two antibodies selected from the group of antibodies consisting of MOC-31, Ber-EP 4 and 8B6, whereby testicular tumor cells are detected in the sample.

14. The method according claim 1, further comprising testing a combination of mRNA portions which combination comprises mRNA portions corresponding to sequence portions of at least two genes selected from the group consisting of GA733.2, EGER, CEA, HER2/neu, claudin-7 (CLDN7), GCAP (ALPPL2)/ALPP, GRPR, HMGIC, CK20, MAGE3, MUC1 and stanniocalcin (STCI), whereby cells of a specific tumor type or subtype are detected.

15. The method according to claim 14, wherein the combination of mRNA portions comprises mRNA portions corresponding to sequence portions of at least two genes selected from the group consisting of EGFR, GA733.2 and HER2/NEU, where cells of a specific tumor type or subtype are detected.

16. The method according to claim 14, wherein the combination of mRNA portions comprises mRNA portions corresponding to sequence portions of at least two genes selected from the group consisting of GA733.2, MUC1, Her-2/neu, claudin 7, CK20, MAGE-3, stanniocalcin, EGFR and CEA, whereby breast tumor cells are detected.

17. The method according to claim 14, wherein the combination of mRNA portions comprises mRNA portions corresponding to sequence portions of (a) the genes GA733.2 and MUC1, (b) the genes Her-2/neu and claudin 7, (c) at least two genes selected from the group consisting of CK20, MAGE-3 and MUC1, and/or (d) at least two genes selected from the group consisting of stanniocalcin, EGFR and CEA, whereby breast tumor cells are detected.

18. The method according to claim 14, wherein the combination of mRNA portions comprises mRNA portions corresponding to sequence portions of at least two genes selected from the group consisting of CK20, EGFR, GA733.2, CEA and stanniocalcin, whereby colon tumor cells are detected.

19. The method according to claim 18, wherein the combination of mRNA portions comprises mRNA portions corresponding to sequence portions of (a) at least two genes selected from the group consisting of CK20, EGFR, CEA and stanniocalcin and/or (b) at lest two genes selected from the group consisting of EGFR, CEA and GA733.2, whereby colon tumor cells are detected.

20. The method according to claim 14, wherein the combination of mRNA portions comprises mRNA portions corresponding to sequence portions of at least two genes selected from the group consisting of ALPP/ALPPL2 (GCAP), GA733.2 (=EGP-40), HMGI-C, and GRPR, whereby testicular tumor cells are detected.

21. The method according to claim 1, wherein the mRNA portions are multiplied and/or detected using polymerase chain reaction (PCR), LCR, NASBA, RT-PCR and/or hybridization methods.

22. The method according to claim 1, further comprising reverse transcribing the mRNA of the separated cells into cDNA, multiplying the cDNA and subsequently detecting the presence or absence of the mRNA portion to be detected.

23. The method according to claim 22, further comprising digesting the multiplied cDNA by restriction enzymes to produce cDNA fragments, and detecting the presence or absence of the mRNA to be detected by means of the produced cDNA fragments.

24. The method according to claim 22, wherein the cDNA corresponding to the mRNA to be detected is determined by means of fluorescence-based real time-PCR.

25. The method according to claim 1, wherein the mRNA that codes for the protein β-actin is detected as an internal control.

26. The method according to claim 1, wherein the separation of the marked cell is effected with a solid phase.

* * * * *

UNITED STATES PATENT AND TRADEMARK OFFICE
CERTIFICATE OF CORRECTION

| | | |
|---|---|---|
| PATENT NO. | : 7,507,528 B2 | Page 1 of 1 |
| APPLICATION NO. | : 10/488729 | |
| DATED | : March 24, 2009 | |
| INVENTOR(S) | : Winfried Albert et al. | |

It is certified that error appears in the above-identified patent and that said Letters Patent is hereby corrected as shown below:

In claim 14, column 23, line 53, delete "EGER" and insert --EGFR-- therefor.

Signed and Sealed this

Second Day of June, 2009

JOHN DOLL
*Acting Director of the United States Patent and Trademark Office*

SEQUENCE LISTING

```
<160> NUMBER OF SEQ ID NOS: 26

<210> SEQ ID NO 1
<211> LENGTH: 24
<212> TYPE: DNA
<213> ORGANISM: Artificial
<220> FEATURE:
<223> OTHER INFORMATION: DNA primer sequence

<400> SEQUENCE: 1
aatcgtcaat gccagtgtac ttca                                          24
```

```
<210> SEQ ID NO 2
<211> LENGTH: 24
<212> TYPE: DNA
<213> ORGANISM: Artificial
<220> FEATURE:
<223> OTHER INFORMATION: DNA primer sequence

<400> SEQUENCE: 2
taacgcgttg tgatctcctt ctga                                          24

<210> SEQ ID NO 3
<211> LENGTH: 24
<212> TYPE: DNA
<213> ORGANISM: Artificial
<220> FEATURE:
<223> OTHER INFORMATION: DNA primer sequence

<400> SEQUENCE: 3
agtcgggctc tggaggaaaa gaaa                                          24

<210> SEQ ID NO 4
<211> LENGTH: 24
<212> TYPE: DNA
<213> ORGANISM: Artificial
<220> FEATURE:
<223> OTHER INFORMATION: DNA primer sequence

<400> SEQUENCE: 4
gatcataatt cctctgcaca tagg                                          24

<210> SEQ ID NO 5
<211> LENGTH: 24
<212> TYPE: DNA
<213> ORGANISM: Artificial
<220> FEATURE:
<223> OTHER INFORMATION: DNA primer sequence

<400> SEQUENCE: 5
agaaatgacg caagagccta tgta                                          24

<210> SEQ ID NO 6
<211> LENGTH: 24
<212> TYPE: DNA
<213> ORGANISM: Artificial
<220> FEATURE:
<223> OTHER INFORMATION: DNA primer sequence

<400> SEQUENCE: 6
aacttgtgtg tgttgctgcg gtat                                          24

<210> SEQ ID NO 7
<211> LENGTH: 24
<212> TYPE: DNA
<213> ORGANISM: Artificial
<220> FEATURE:
<223> OTHER INFORMATION: DNA primer sequence

<400> SEQUENCE: 7
tcagcttcta ctctggtgca caac                                          24

<210> SEQ ID NO 8
<211> LENGTH: 24
<212> TYPE: DNA
<213> ORGANISM: Artificial
<220> FEATURE:
<223> OTHER INFORMATION: DNA primer sequence
```

```
<400> SEQUENCE: 8
tggtagtagt cggtgctggg atct                                              24

<210> SEQ ID NO 9
<211> LENGTH: 24
<212> TYPE: DNA
<213> ORGANISM: Artificial
<220> FEATURE:
<223> OTHER INFORMATION: DNA primer sequence

<400> SEQUENCE: 9
cccagtgtgt caactgcagc cagt                                              24

<210> SEQ ID NO 10
<211> LENGTH: 24
<212> TYPE: DNA
<213> ORGANISM: Artificial
<220> FEATURE:
<223> OTHER INFORMATION: DNA primer sequence

<400> SEQUENCE: 10
cagatgggca tgtaggagag gtca                                              24

<210> SEQ ID NO 11
<211> LENGTH: 24
<212> TYPE: DNA
<213> ORGANISM: Artificial
<220> FEATURE:
<223> OTHER INFORMATION: DNA primer sequence

<400> SEQUENCE: 11
gtcttgccgc cttggtagct tgct                                              24

<210> SEQ ID NO 12
<211> LENGTH: 24
<212> TYPE: DNA
<213> ORGANISM: Artificial
<220> FEATURE:
<223> OTHER INFORMATION: DNA primer sequence

<400> SEQUENCE: 12
tggacttagg gtaagagcgg ggtg                                              24

<210> SEQ ID NO 13
<211> LENGTH: 24
<212> TYPE: DNA
<213> ORGANISM: Artificial
<220> FEATURE:
<223> OTHER INFORMATION: DNA primer sequence

<400> SEQUENCE: 13
gccacgcagc tcatctccaa catg                                              24

<210> SEQ ID NO 14
<211> LENGTH: 24
<212> TYPE: DNA
<213> ORGANISM: Artificial
<220> FEATURE:
<223> OTHER INFORMATION: DNA primer sequence

<400> SEQUENCE: 14
atgatcgtct cagtcagtgc ccgg                                              24

<210> SEQ ID NO 15
<211> LENGTH: 24
```

```
<212> TYPE: DNA
<213> ORGANISM: Artificial
<220> FEATURE:
<223> OTHER INFORMATION: DNA primer sequence

<400> SEQUENCE: 15
tctccccgtg aacgatgact ggtc                                          24

<210> SEQ ID NO 16
<211> LENGTH: 24
<212> TYPE: DNA
<213> ORGANISM: Artificial
<220> FEATURE:
<223> OTHER INFORMATION: DNA primer sequence

<400> SEQUENCE: 16
tgaagacaga caccccaaca gagg                                          24

<210> SEQ ID NO 17
<211> LENGTH: 24
<212> TYPE: DNA
<213> ORGANISM: Artificial
<220> FEATURE:
<223> OTHER INFORMATION: DNA primer sequence

<400> SEQUENCE: 17
aaaggcagca aaacaagag tccc                                           24

<210> SEQ ID NO 18
<211> LENGTH: 24
<212> TYPE: DNA
<213> ORGANISM: Artificial
<220> FEATURE:
<223> OTHER INFORMATION: DNA primer sequence

<400> SEQUENCE: 18
ccaactgctg ctgaggtaga aatc                                          24

<210> SEQ ID NO 19
<211> LENGTH: 24
<212> TYPE: DNA
<213> ORGANISM: Artificial
<220> FEATURE:
<223> OTHER INFORMATION: DNA primer sequence

<400> SEQUENCE: 19
atctccaagg cctgaataag gtct                                          24

<210> SEQ ID NO 20
<211> LENGTH: 25
<212> TYPE: DNA
<213> ORGANISM: Artificial
<220> FEATURE:
<223> OTHER INFORMATION: DNA primer sequence

<400> SEQUENCE: 20
cctcagttcc ttttaattct tcagt                                         25

<210> SEQ ID NO 21
<211> LENGTH: 24
<212> TYPE: DNA
<213> ORGANISM: Artificial
<220> FEATURE:
<223> OTHER INFORMATION: DNA primer sequence

<400> SEQUENCE: 21
```

```
ctccagcctc cccactacca tgaa                                              24

<210> SEQ ID NO 22
<211> LENGTH: 24
<212> TYPE: DNA
<213> ORGANISM: Artificial
<220> FEATURE:
<223> OTHER INFORMATION: DNA primer sequence

<400> SEQUENCE: 22
ttgtcaccca gcaggccatc gtag                                              24

<210> SEQ ID NO 23
<211> LENGTH: 24
<212> TYPE: DNA
<213> ORGANISM: Artificial
<220> FEATURE:
<223> OTHER INFORMATION: DNA primer sequence

<400> SEQUENCE: 23
aacccatgag gcggagcaga atga                                              24

<210> SEQ ID NO 24
<211> LENGTH: 24
<212> TYPE: DNA
<213> ORGANISM: Artificial
<220> FEATURE:
<223> OTHER INFORMATION: DNA primer sequence

<400> SEQUENCE: 24
cgttggcgat gcattttaag ctct                                              24

<210> SEQ ID NO 25
<211> LENGTH: 24
<212> TYPE: DNA
<213> ORGANISM: Artificial
<220> FEATURE:
<223> OTHER INFORMATION: DNA primer sequence

<400> SEQUENCE: 25
ctggagaaga gctacgagct gcct                                              24

<210> SEQ ID NO 26
<211> LENGTH: 24
<212> TYPE: DNA
<213> ORGANISM: Artificial
<220> FEATURE:
<223> OTHER INFORMATION: DNA primer sequence

<400> SEQUENCE: 26
acaggactcc atgcccagga agga                                              24
```